United States Patent
Schock et al.

[11] Patent Number: 6,024,693
[45] Date of Patent: Feb. 15, 2000

[54] INTRA-AORTIC BALLOON CATHETER

[75] Inventors: Robert Schock, Sparta; Olga Laksin, Scotch Plains; Manuel Marques, Newark, all of N.J.

[73] Assignee: Datascope Investment Corp., Montvale, N.J.

[21] Appl. No.: 09/174,279

[22] Filed: Oct. 16, 1998

[51] Int. Cl.[7] .................................................. A61N 1/362
[52] U.S. Cl. ........................................... 600/18; 604/96
[58] Field of Search ........................ 604/96, 915, 917, 604/265; 427/2.1; 606/192, 194; 600/16, 18

[56] References Cited

U.S. PATENT DOCUMENTS

| | | |
|---|---|---|
| 4,213,461 | 7/1980 | Pevsner . |
| 4,239,729 | 12/1980 | Hasegawa et al. ................ 422/48 |
| 5,135,516 | 8/1992 | Sahatjian et al. ............... 604/265 |
| 5,176,661 | 1/1993 | Evard et al. .................... 604/282 |
| 5,190,520 | 3/1993 | Fenton, Jr. et al. ............... 604/43 |
| 5,192,296 | 3/1993 | Bhate et al. .................... 606/194 |
| 5,370,615 | 12/1994 | Johnson ......................... 604/96 |
| 5,382,234 | 1/1995 | Cornelius et al. ................. 604/96 |
| 5,423,764 | 6/1995 | Cornelius et al. ................ 604/103 |
| 5,456,665 | 10/1995 | Postell et al. .................... 604/96 |
| 5,460,607 | 10/1995 | Miyata et al. .................... 604/96 |
| 5,514,073 | 5/1996 | Miyata et al. ..................... 60/18 |
| 5,711,754 | 1/1998 | Miyata et al. .................... 600/18 |
| 5,827,229 | 10/1998 | Auth et al. ...................... 604/171 |
| 5,833,672 | 11/1998 | Kawata et al. ................... 604/280 |
| 5,833,706 | 11/1998 | St. Germaine et al. ............. 606/194 |
| 5,879,324 | 3/1999 | Von Hoffmann ................... 604/49 |

FOREIGN PATENT DOCUMENTS

| | | |
|---|---|---|
| 0380102 | 8/1990 | European Pat. Off. ........ A61M 29/02 |
| 638327A1 | 2/1995 | European Pat. Off. ........ A61M 29/02 |
| WO 95/17219 | 6/1995 | WIPO .............................. A61M 5/32 |
| WO 97/18005 | 5/1997 | WIPO ............................ A61M 25/00 |

OTHER PUBLICATIONS

Copy of Datascope Marketing Material for Pecor STat DL 8.5 FR 40cc coextuded catheter, 4 pages, Datascope Copyright 1991.

*Primary Examiner*—Mark Bockelman
*Attorney, Agent, or Firm*—Abraham P. Ronai

[57] ABSTRACT

An improved intra-aortic balloon catheter with a balloon membrane, a tip, and a co-lumen extruded tube having an outer lumen and an inner lumen between the inner and outer surfaces of the co-lumen extruded tube. The portion of the co-lumen extruded tube that defines the inner lumen and which is disposed within the balloon membrane is made from polyimide, a lubricous material, to facilitate guide wire tracking. The polyimide inner tube portion demonstrates good kink resistance and flexural stiffness. In a first alternative embodiment of the invention the co-lumen tube comprises an outer tube with an inner tube embedded in the wall of said outer tube. In a second alternative embodiment of the invention a longitudinal signal pathway is provided.

17 Claims, 4 Drawing Sheets

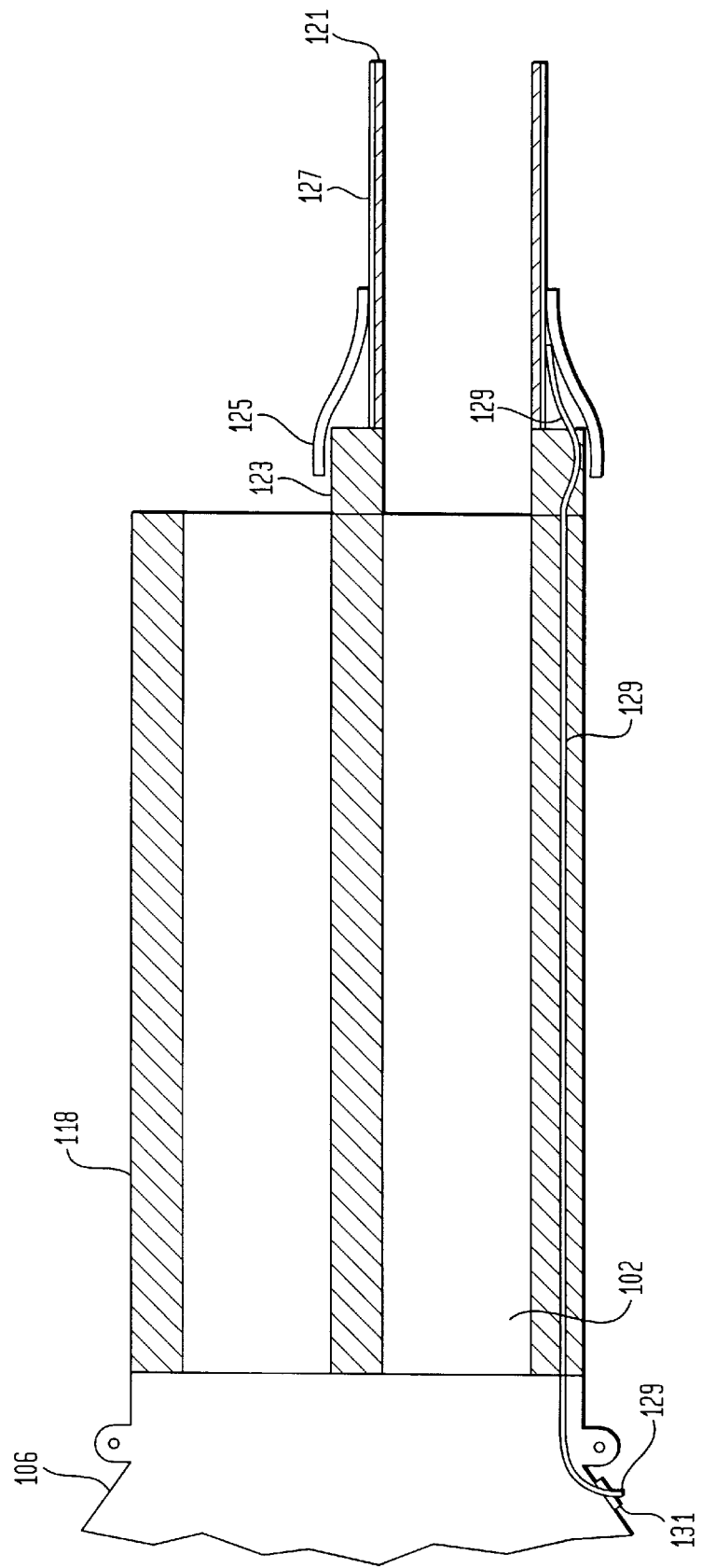

INTRA-AORTIC BALLOON CATHETER

BACKGROUND OF THE INVENTION

1. Field of the Invention

The invention relates to an improved intra-aortic balloon catheter. More particularly, the invention relates to an intra-aortic balloon catheter having an improved catheter body and an improved kink-resistant inner tube that demonstrates improved guide wire tracking.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body. A passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heart beat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

IAB catheters may also have a central passageway or lumen which can be used to measure aortic pressure. Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon. In this dual lumen construction, the central lumen may also be used to accommodate a guide wire to facilitate placement of the IAB catheter and to infuse fluids, or to do blood sampling.

Very specialized materials, including Nitinol, have been used for the inner tube in an effort to reduce its outer diameter. A reduced diameter inner tube allows for a reduced diameter of the folded IAB membrane and thus allows for an easier insertion of the IAB catheter into the patient. The benefits of Nitinol include its high kink resistance and flexural stiffness at small wall thicknesses compared to the traditional polyurethane material used for prior art inner tubes. One major problem with Nitinol, however, is its high cost. Therefore, the need exists for an inner tube that is economical to manufacture and that has good kink resistance and flexural stiffness.

Another materials related problem encountered with dual lumen IAB catheters involves advancing the IAB catheter over the guide wire into the patient and also withdrawing the guide wire from the central tube after final placement of the IAB catheter. Friction between the outer surface of the guide wire and the inner surface of the central tube makes it difficult for the IAB catheter to track the guide wire. Therefore, the need exists for an IAB catheter, having an inner tube with a low coefficient of friction, that demonstrates improved guide wire tracking.

Co-pending U.S. patent application Ser. No. 08/958004 discloses an intra-aortic balloon catheter having a co-lumen extruded tube in which the inner lumen lies between the inner and outer surfaces of the catheter tube. As disclosed in that application a co-lumen arrangement allows for an increased gas path area. It is currently desired to achieve the same increase in gas path area but to allow for an inner tube which is made from a different material. Choice of a different material for the inner tube will allow for greater control of the kink resistance and flexural stiffness of said inner tube and of the entire catheter.

U.S. Pat. No. 5,711,754 by Miyata et al., discloses a balloon catheter having an inner tube affixed to the inner wall of the catheter tube by adhesion, melt-bonding, or integral formation. When affixed by integral formation, however, the catheter tube and the inner tube are comprised of the same material.

Yet another problem encountered with dual lumen IAB catheters is diffusion of gas or fluid from the outer lumen into the inner lumen. Any adulteration of the fluid within the inner lumen may corrupt blood pressure readings. Typically, the outer lumen of an IAB catheter contains a gas, such as Helium, and the inner lumen contains an incompressible column of fluid, such as saline, used for blood pressure measurements. The distal end of the saline column is in contact with the patient's blood and the proximal end of the column is in contact with a pressure transducer. The pressure reading of the pressure transducer correlates to the blood pressure of the patient. Any diffusion of a gas into the inner lumen increases the compressibility of the saline column thus affecting the blood pressure reading. Therefore, there is a need for a catheter designed to measure blood pressure without the aid of a potentially adulterated saline column.

While the IAB catheters presently on the market may be suitable for the particular purpose employed, or for general use, they would not be as suitable for the purposes of the present invention as disclosed hereafter.

SUMMARY OF THE INVENTION

Accordingly, it is an object of the invention to produce an improved IAB catheter capable of improved guide wire tracking.

It is another object of the invention to produce an improved IAB catheter having an inner tube that is economical to manufacture and that has good kink resistance and flexural stiffness.

It is yet another object of the invention to produce an improved IAB catheter having a co-lumen catheter body with an increased effective gas path area and which allows for an inner tube made from a different material than the catheter body.

It is still yet another object of the invention to produce an improved IAB catheter capable of accurate blood pressure measurements.

The invention is an improved intra-aortic balloon catheter with a balloon membrane, a tip, and a co-lumen extruded tube having an outer lumen and an inner lumen between the inner and outer surfaces of the co-lumen extruded tube. The portion of the co-lumen extruded tube that defines the inner lumen and which is disposed within the balloon membrane is made from polyimide, a lubricous material, to facilitate guide wire tracking. The polyimide inner tube portion demonstrates good kink resistance and flexural stiffness. In a first alternative embodiment of the invention the co-lumen tube comprises an outer tube with an inner tube embedded in the wall of said outer tube. In a second alternative embodiment of the invention a longitudinal signal pathway is provided.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 5 is a longitudinal cross section of a second alternative embodiment of the improved IAB catheter shown without the balloon membrane and the tip and with only the distal portion of the connector.

DETAILED DESCRIPTION OF THE PREFERRED EMBODIMENTS

Figure 1:
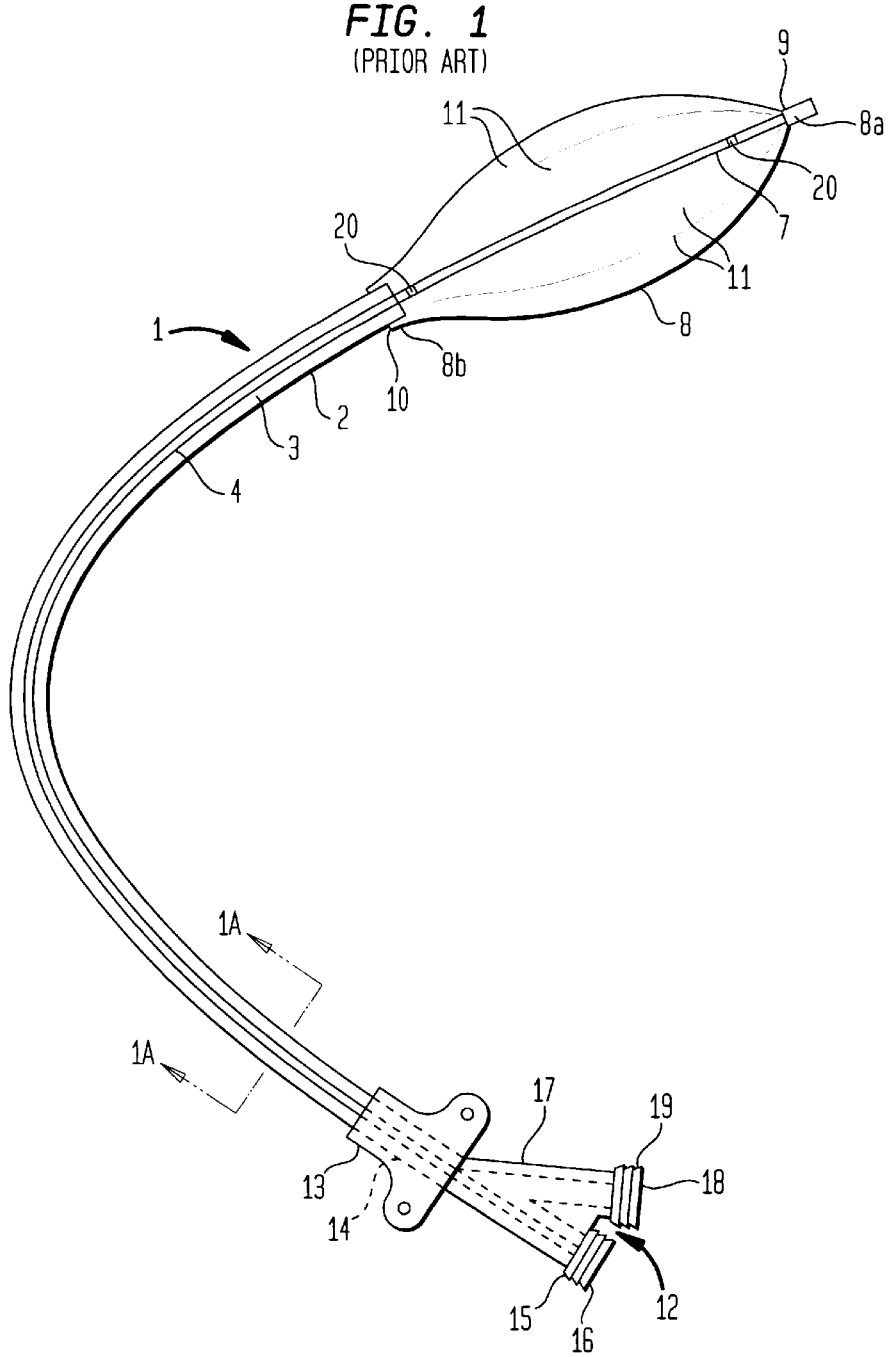
FIG. 1 is a longitudinal cross section of a prior art intra-aortic balloon catheter.
Figure 1A:
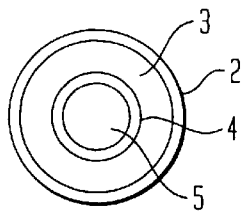
FIG. 1A is a transverse cross section of the prior art catheter of FIG. 1 taken along lines 1A—1A.

The general structure of an intra-aortic balloon catheter is best described in relation to FIGS. 1 and 1A which illustrate a dual-lumen prior art intra-aortic balloon catheter. The catheter 1 is constructed of a clear plastic outer tube 2 forming a gas passageway lumen 3; and another clear plastic central tube 4 disposed within outer tube 2 and creating a central passageway or lumen 5 as may best be seen in FIG. 1A.

Note that the proximal and distal directions are relative to the heart. Therefore, the further distal a portion of a catheter is the closer it is to the heart after insertion of the catheter.

A balloon 8 is disposed at the distal end of the catheter 1. The distal portion 7 of the central tube 4 extends beyond the distal end 10 of outer tube 2. The distal end 8A of the balloon 8 is attached to a tip 9 formed on the distal end 7 of central tube 4. The proximal end 8B of the balloon 8 is attached to the distal end 10 of the outer tube 2. The distal portion 7 of the central tube 4 supports the balloon 8. Said distal portion 7 must have sufficient strength to prevent inversion of the balloon 8 as it inflates and deflates under aortic pressure, but at the same time, be flexible enough to be safely inserted through an introducer sheath, moved through the arterial tree, and maintained in the thoracic aorta.

The balloon 8 is formed of a nonthrombogenic flexible material, such as polyurethane, and may have folds 11 formed as a result of wrapping the balloon 8 about the central tube 4 to ease insertion of the catheter 1. Radioopaque bands 20 at the distal end of the catheter 1 aid in positioning the balloon 8 in the descending aorta.

Inflation and deflation of the balloon 8 is accomplished through the gas passageway lumen 3. The central passageway or lumen 5 can accommodate a guide wire for placement or repositioning of the catheter 1. When the guide wire is not disposed in the central lumen 5, the central lumen 5 may be used for measuring blood pressure in the descending aorta. This pressure measurement may be used to coordinate the inflation and deflation of the balloon 8 with the pumping of the heart, however, use of the patient's ECG is preferred. Additionally, the central lumen 5 may be used to infuse liquids into the descending aorta, or to sample blood.

At the proximal end 12 of the catheter 1 a hub 13 is formed on the proximal end 14 of the outer tube 2. The central passageway or lumen 5 extends through the hub 13 and a connector 16 is provided at the proximal end 15 (or exit) of the central passageway or lumen 5. Measurement of aortic pressure and blood sampling may be done through the proximal end 15 of the central passageway 5.

The proximal end 18 of the gas passageway lumen 3 exits through a side arm 17 of the hub 13 on which is provided a connector 19. The proximal end 18 of the central passageway or lumen 5 may be connected to an intra-aortic balloon pump.

Figure 2:
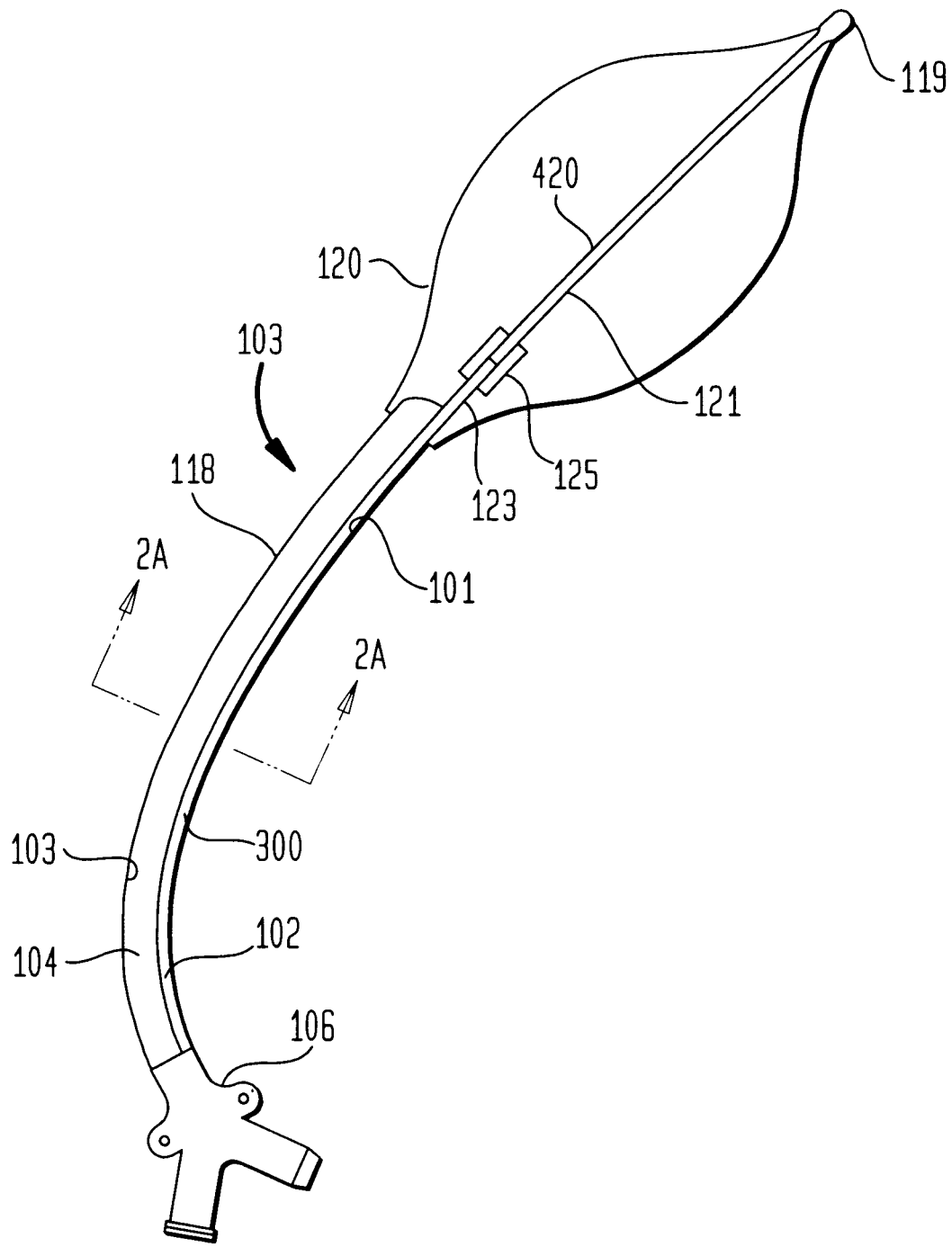
FIG. 2 is a longitudinal cross section of an improved catheter.

FIG. 2 illustrates an embodiment of an improved IAB catheter, generally designated 103. "An extruded co-lumen tube 118" having distal and proximal ends, is connected on its distal end to a proximal end of a balloon membrane 120 and on its proximal end to a connector 106. An inner tube portion 123 extends beyond the distal end of the co-lumen tube 118 and is enveloped by the balloon membrane 120. A proximal end of an inner lumen extension tube 121 is attached to a distal end of the inner tube portion 123 by means of a crimp 125. A distal end of the inner lumen extension tube 121 is attached to a tip 119. Said tip 119 is attached to a distal end of the balloon membrane 120. A portion of the distal end of the inner lumen extension tube 121, which is attached to the tip 119, and a portion of the proximal end of the inner lumen extension tube 121, which is attached to the co-lumen tube 118, may each have a reduced wall thickness so as to prevent any restriction of gas flow and to assure a sufficiently small outer diameter of the tip 119.

The inner lumen extension tube 121 should be made from a material, such as, but not limited to polyester, polycarbonate, polyolefine, and polyimide. The inner lumen extension tube 121 may be coated with polyurethane to facilitate its bond to the columen extruded tube 118 and the tip 119. The lubricity of the polyimide inner lumen extension tube 121 allows the intra-aortic balloon catheter to track a guide wire with ease.

Figure 3:
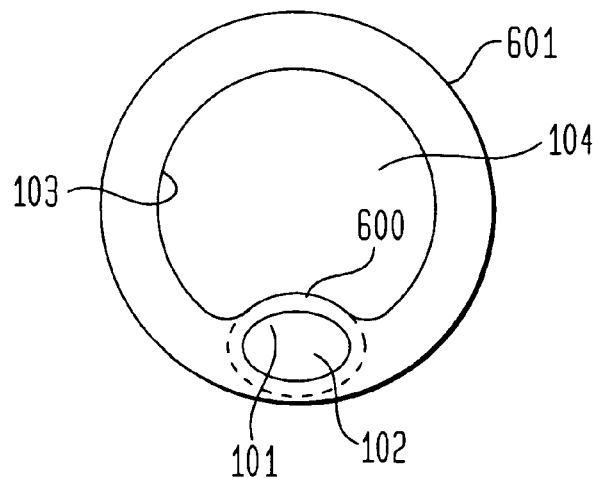
FIG. 3 is a transverse cross section of the improved catheter of FIG. 2 taken along lines 2A—2A.

FIG. 3 illustrates a transverse cross section of the co-lumen tube 118 illustrated in FIG. 2 taken along lines 2A—2A comprising an inner tube section 600 and an outer tube section 601. An outer lumen 104 is defined by a first inner surface 103. An inner lumen 102 extends the entire length of the co-lumen tube 118 and the inner lumen extension tube 121. A first portion 300 of the inner lumen 102 is defined by a second inner surface 101 of the co-lumen tube 118. A second portion 301 of the inner lumen 102 communicates with the first portion 300 of the inner lumen 102 and is defined by an inner surface 420 of the inner lumen extension tube 121. The second inner surface 101 and the inner surface 420 of the inner lumen extension tube 121 may be coated with a hydrophilic coating, such as a Hydromer coating, to reduce the retention of gas bubbles within the inner lumen 102. Gas bubbles are known to degrade the quality of blood pressure signals measured through the inner lumen 102. The inner tube section 600 and the outer tube section 601 may be made of the same or different materials. If different materials are chosen the inner tube section 600 should be made from a softer material, such as, but not limited to, polyurethane, silicone elastomer, EPDM rubber, or polyetheramide.

Given a sufficient wall thickness the polyimide inner lumen extension tube 121 will provide good kink resistance and stiffness. The wall thickness of the polyimide inner lumen extension tube 121 should range between 0.004" and 0.010" and the inner diameter of the inner lumen extension tube 121 should range between 0.020" and 0.035". The properly sized polyimide inner lumen extension tube 121 has sufficient strength to prevent inversion of the balloon membrane 120 as it inflates and deflates under aortic pressure, and at the same time, is flexible enough to be safely inserted through an introducer sheath, moved through the arterial tree, and maintained in the thoracic aorta. Note that the inner surface 420 of the inner lumen extension tube 121 may be lined with a biocompatible polymer, such as "polytetraflouraethylene, or for example" TEFLON (TEFLON is a trademark of Dupont Corp.), to reduce friction against the guidewire and improve biocompatibility, or may be lined with a heparin-based coating, such as DURAFLO (DURAFLO is a trademark of Baxter International Corp.), to specifically improve biocompatibility.

Figure 4:
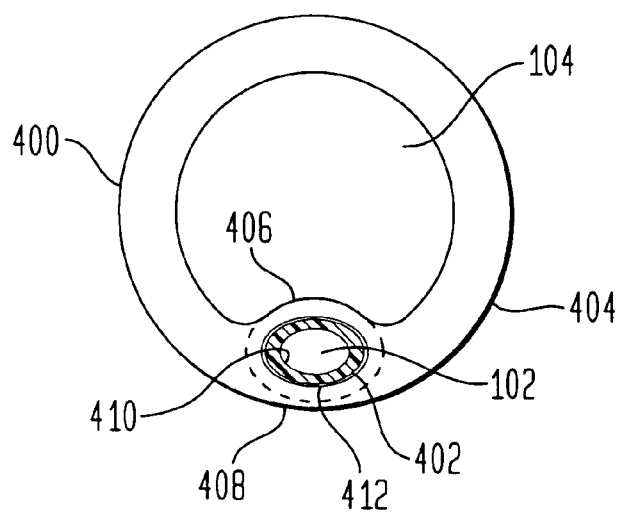
FIG. 4 is a transverse cross section of a first alternative embodiment of the co-lumen extruded tube.

A first alternative embodiment of the invention comprises an alternate co-lumen tube, generally designated 400, in FIG. 4. FIG. 4 illustrates a transverse cross section of the co-lumen tube 400. The co-lumen tube 400 comprises an inner tube 402 having an inner surface 410 and an outer surface 412 and an outer tube 404 having an inner surface 406 and an outer surface 408. The inner tube 402 is completely embedded in the wall of the outer tube 404 such that the inner tube 402 lies between the inner surface 406 and the outer surface 408 of the outer tube 404. The inner surface 410 of the inner tube 402 defines an inner lumen 102 and the inner surface 406 of the outer tube 404 defines an outer lumen 104. The inner tube 402 extends longitudinally from the proximal end (not shown) of the outer tube 404 to the tip (not shown). Both the inner tube 402 and the outer tube 404 can be made of the same or different materials. If different materials are chosen the outer tube 404 should be made from a softer material, such as, but not limited to, polyurethane, silicone elastomer, EPDM rubber, or polyetheramide, and the inner tube 402 should be made from a harder material, such as, but not limited to, polyester, polycarbonate, polyolefine, and polyimide. Similar to the inner lumen extension tube 121, as illustrated FIG. 2, the inner tube 402 may have an outer coating of polyurethane to facilitate bonding with a tip. Furthermore, the inner tube 402 may have an inner coating of a hydrophilic coating, such as a Hydromer coating, to reduce the retention of gas bubbles in the central tube. Gas bubbles, as described above, are known to degrade the quality of blood pressure measurements. Note that the inner surface 410 of the inner tube 402 may be lined with a biocompatible polymer, such as TEFLON (TEFLON is a trademark of Dupont Corp.), to reduce friction against the guidewire and improve biocompatibility, or may be lined with a heparin-based coating, such as DURAFLO (DURAFLO is a trademark of Baxter International Corp.), to specifically improve biocompatibility.

FIG. 5 illustrates a longitudinal cross sectional view of a second alternative embodiment of the improved intra-aortic balloon catheter shown without the balloon membrane 120 and the tip 119. For clarity only a distal portion of the connector 106 is shown. The inner lumen extension tube 121 is coated with a conductive coating 127, such as metal, including platinum, gold, and silver. Note that the term "coated" as herein used intends to encompass any type of coating including a full, partial, or selective coating. A first wire 129 embedded in the wall of the co-lumen extruded tube 118 extending substantially the entire length of the intra-aortic balloon catheter contacts the proximal end of the inner lumen extension tube 121 and terminates at a connecting site 131. The crimp 125 maintains contact between the first wire 129 and the inner lumen extension tube 121. Note that the outer diameter of the inner lumen extension tube 121 is smaller than the outer diameter of the inner tube portion 123 and that the inner diameter of the inner lumen extension tube 121 is the same as the inner diameter of the inner tube portion 123. Note further that a second wire (not shown), embedded in the wall of the inner lumen extension tube 121 and extending its entire length, may be substituted for the conductive coating 127.

The distal end of the inner lumen extension tube 121 is attached to the tip 119 (not shown) which contains a measuring device such as a pressure transducer. Any signal generated by the measuring device is communicated along the conductive coating 127 of the inner lumen extension tube 121 (or alternatively along the second wire (not shown) embedded in the wall of the inner lumen extension tube 121) to the first wire 129 and finally to a monitoring or recording device which attaches at the connecting site 131 to the first wire 129. If there is a need to monitor more than one signal multiple wires can be embedded in the intra-aortic balloon catheter or in the inner lumen extension tube 121. Multiple coatings on the inner lumen extension tube 121, coated one on top of the other with nonconductive coatings separating said conductive coatings, or longitudinal coating strips may also be used to communicate multiple signals. Using the conductive coating 127 and the first wire 129 to communicate blood pressure or other vital sign information to a monitoring device rather than a column of saline eliminates the problem of Helium adulteration of the saline column affecting measurements. Note that the use of a conductive coating or wires, to communicate signals from one end of the catheter to the opposite end, is also anticipated for conventional IAB catheters.

A third alternative embodiment of the invention comprises a co-axial catheter having a central tube made from polyimide. The alternative embodiment is identical to the prior art catheter 1, as illustrated in FIG. 1, however, with the central tube 4 made from polyimide. Similar to the inner lumen extension tube 121, illustrated FIG. 2, the polyimide central tube may have an outer coating of polyurethane to facilitate bonding with a tip. The lubricity of the polyimide material allows the co-axial intra-aortic balloon catheter to track a guide wire with ease. Furthermore, the central tube may have an inner coating of a hydrophilic coating, such as a Hydromer coating, to reduce the retention of gas bubbles in the central tube. Gas bubbles, as described above, are known to degrade the quality of blood pressure measurements. Note that the inner surface of the central tube may be also lined with a biocompatible polymer, such as TEFLON (TEFLON is a trademark of Dupont Corp.), to reduce friction against the guidewire and improve biocompatibility, or may be lined with a heparin-based coating, such as DURAFLO (DURAFLO is a trademark of Baxter International Corp.), to specifically improve biocompatibility.

What is claimed is:

1. A balloon catheter comprising a co-lumen tube having a proximal end and a distal end, a balloon membrane having a proximal end and a distal end, and an inner lumen extension tube, said inner lumen extension tube having a proximal end, a distal end, an outer surface, and an inner surface defining a second portion of an inner lumen, said co-lumen tube having a first inner surface, defining an outer lumen, and a second inner surface, defining a first portion of the inner lumen, the proximal end of the inner lumen extension tube is connected to the distal end of the co-lumen tube, the distal end of the inner lumen extension tube is attached to a tip, said tip is attached to the distal end of the balloon membrane, the proximal end of the balloon membrane is attached to the distal end of the co-lumen tube, at least a portion of the inner lumen extension tube is disposed within the balloon membrane, the second portion of the inner lumen communicates with the first portion of the inner lumen, the inner lumen extends the entire length of the co-lumen tube and the entire length of the inner lumen extension tube, the outer lumen extends substantially the length of the co-lumen tube, the outer lumen and the first portion of the inner lumen are not concentric.

2. The balloon catheter as claimed in claim 1 wherein at least a portion of the outer surface of the inner lumen extension tube is coated with polyurethane.

3. The balloon catheter as claimed in claim 1 wherein at least a portion of the inner surface of the inner lumen extension tube is coated with a biocompatible polymer.

4. The balloon catheter as claimed in claim 1 wherein at least a portion of the inner surface of the inner lumen extension tube is coated with a heparin-based material.

5. The balloon catheter as claimed in claim 1 wherein the inner lumen extension tube is made from polyimide.

6. The balloon catheter as claimed in claim 1 wherein the inner surface of the inner lumen extension tube is coated with polytetraflouraethylene.

7. The balloon catheter as claimed in claim 1 wherein the inner lumen extension tube has a wall thickness between about 0.004" and about 0.006" and an inner diameter between about 0.020" and about 0.035".

8. The balloon catheter as claimed in claim 1 wherein the inner lumen extension tube is substantially enveloped by the balloon membrane.

9. The balloon catheter as claimed in claim 1 wherein the inner lumen extension tube is at least partially disposed within the second inner surface of the first tube.

10. The balloon catheter as claimed in claim 9 wherein the inner lumen extension tube and the first tube are made from different materials.

11. The balloon catheter as claimed in claim 1 wherein the inner lumen extension tube and the first tube are made from different materials.

12. A balloon catheter comprising a co-lumen tube having a proximal end and a distal end, a balloon membrane having a proximal end and a distal end, and an inner lumen extension tube, said inner lumen extension tube having a proximal end, a distal end, an outer surface, and an inner surface, defining a second portion of an inner lumen, said co-lumen tube having a first inner surface, defining an outer lumen, and a second inner surface, defining a first portion of the inner lumen, the inner lumen extension tube being at least partially disposed within the second inner surface of the co-lumen tube, the distal end of the inner lumen extension tube is attached to a tip, said tip is connected to the distal end of the balloon membrane, the proximal end of the balloon membrane is attached to the distal end of the co-lumen tube, at least a portion of the inner lumen extension tube is disposed within the balloon membrane, the inner lumen extends substantially the entire length of the catheter, the outer lumen extends substantially the length of the co-lumen tube, the inner lumen extension tube is made from polyimide, the outer lumen and the first portion of the inner lumen are not concentric.

13. The balloon catheter as claimed in claim 12 wherein at least a portion of the outer surface of the inner lumen extension tube is coated with polyurethane.

14. The balloon catheter as claimed in claim 12 wherein at least a portion of the inner surface of the inner lumen extension tube is coated with a biocompatible polymer.

15. The balloon catheter as claimed in claim 12 wherein at least a portion of the inner surface of the inner lumen extension tube is coated with a heparin-based material.

16. The balloon catheter as claimed in claim 12 wherein at least a portion of the inner lumen extension tube is coated with polytetraflouraethylene.

17. The balloon catheter as claimed in claim 12 wherein the inner lumen extension tube has a wall thickness between about 0.004" and about 0.006" and an inner diameter between about 0.020" and about 0.035".

* * * * *

UNITED STATES PATENT AND TRADEMARK OFFICE
CERTIFICATE OF CORRECTION

PATENT NO : 6,024,693
DATED : February 15, 2000
INVENTOR(S) : Schock, et al

It is certified that an error appears in the above-identified patent and that said Letters Patent is hereby corrected as shown below:

On the title page, second column, under OTHER PUBLICATIONS, please change "Pecor STat" to --Percor Stat--.

In claim 9, line 43, column 7, please change "first tube" to --co-lumen tube--.

In claim 10, line 2, column 8, please change "first tube" to --co-lumen tube--.

In claim 11, line 5, column 8, please change "first tube" to --co-lumen tube--.

Signed and Sealed this

Sixth Day of March, 2001

Attest:

NICHOLAS P. GODICI

Attesting Officer

Acting Director of the United States Patent and Trademark Office